(12) United States Patent
Strandberg et al.

(10) Patent No.: US 8,442,647 B2
(45) Date of Patent: May 14, 2013

(54) MEDICAL IMPLANTABLE LEAD AND METHOD FOR THE MANUFACTURE THEREOF

(75) Inventors: Hans Strandberg, Sundbyberg (SE); Åke Sivard, Solna (SE); Åsa Broomé, Hässelby (SE); Kenneth Dahlberg, Stockholm (SE); Gustav Pellijeff, Årsta (SE); Leda Henriquez, Vällingby (SE)

(73) Assignee: St. Jude Medical AB, Jarfalla (SE)

( * ) Notice: Subject to any disclaimer, the term of this patent is extended or adjusted under 35 U.S.C. 154(b) by 49 days.

(21) Appl. No.: 13/132,125

(22) PCT Filed: Dec. 2, 2008

(86) PCT No.: PCT/SE2008/000678
§ 371 (c)(1),
(2), (4) Date: Jun. 1, 2011

(87) PCT Pub. No.: WO2010/064962
PCT Pub. Date: Jun. 10, 2010

(65) Prior Publication Data
US 2011/0245646 A1 Oct. 6, 2011

(51) Int. Cl.
*A61N 1/05* (2006.01)
(52) U.S. Cl.
USPC .......................................... 607/115; 607/127
(58) Field of Classification Search .......... 607/115–119, 607/126–12
See application file for complete search history.

(56) References Cited

U.S. PATENT DOCUMENTS

| 5,545,201 | A | * | 8/1996 | Helland et al. ................ 607/127 |
|---|---|---|---|---|
| 2003/0144718 | A1 | | 7/2003 | Zeijlemaker |
| 2003/0144719 | A1 | | 7/2003 | Zeijlemaker |
| 2004/0014355 | A1 | | 1/2004 | Osypka et al. |
| 2005/0222658 | A1 | | 10/2005 | Hoegh et al. |
| 2008/0132985 | A1 | | 6/2008 | Wedan et al. |
| 2008/0195186 | A1 | | 8/2008 | Li et al. |
| 2009/0149920 | A1 | * | 6/2009 | Li et al. .......................... 607/63 |
| 2009/0171421 | A1 | | 7/2009 | Atalar et al. |

* cited by examiner

*Primary Examiner* — Brian T Gedeon

(57) ABSTRACT

A medical implantable lead adapted to be implanted into a human or animal body for monitoring and/or controlling of an organ inside the body has a fixation in a distal end, which is adapted to fix a distal end of the lead to the organ, an electrode member in the distal end adapted to be in contact with tissue of the organ and receive and/or transmit electrical signals from and/or to the organ, and at least one electrically conducting coil, which includes one or more electrically conducting helical wires and that is adapted to connect the electrode member in the distal end with a monitoring and/or controlling device in a proximal end of the lead. One or more of the individual wires of the coil has a wire core that is provided with a surrounding electrically insulating layer, which in turn is provided with a surrounding electrically conducting shield layer, and the coil is close lapped such that electrically conducting shield layers of adjacent loops of the coil are in electrical contact with each other.

11 Claims, 2 Drawing Sheets

MEDICAL IMPLANTABLE LEAD AND METHOD FOR THE MANUFACTURE THEREOF

BACKGROUND OF THE INVENTION

1. Field of the Invention

The present invention relates to a medical implantable lead of the type adapted to be implanted into a human or animal body for monitoring and/or controlling of an organ inside the body, having a fixation means in a distal end that is adapted to fix the distal end of the lead to the organ, an electrode member in the distal end adapted to be in contact with tissue of the organ and receive and/or transmit electrical signals from and/or to the organ, and at least one electrically conducting coil, which includes one or more electrically conducting helical wires and that is adapted to connect the electrode member in the distal end with a monitoring and/or controlling device in a proximal end of the lead.

The invention also relates to a method for manufacturing of a medical implantable lead.

2. Description of the Prior Art

It is well known in the art to use a medical implantable lead of the above kind to monitor and/or control the function of an organ inside a human or animal body, for example to monitor and/or control a heart by means of a monitoring and/or controlling device in form of a pacemaker or cardiac defibrillator connected to the proximal end of the lead. The medical implantable lead is provided with at least one electrical conductor in form of a coil having one or more helically formed electrical conducting wires. The lead is, in its distal end, provided with one or more electrodes, adapted to be in contact with the tissue of the organ and connected to the one or more electrical conducting coils, for receiving and/or transmitting electrical signals from and/or to the organ. The electrodes can optionally be formed as a contact electrode that abuts against a surface of the organ, as a penetrating electrode that penetrates through a surface of the organ so as to become embedded within the tissue, or as a so-called indifferent electrode that is surrounded by body fluids such as blood.

Normally, such medical implantable leads are not considered to be compatible with Magnetic Resonance Imaging (MRI), i.e. persons or animals having such a lead implanted into the body, are excluded from being examined by MRI scanning. This is due to the fact that the electromagnetic field, that is generated during the MRI scanning, will induce a current in the conductor, which connects the one or more electrodes in the distal end of the medical implantable lead with the monitoring and/or controlling device in the proximal end of the lead. This induced current may cause heating in the electrode that is in contact with the tissue of the organ. If the heating is too high, there is a risk that this will cause damage to the tissue. However, the use of MRI scanning for diagnostics is growing extensively and an increasing number of the population, who have a lead implanted, would benefit from MRI scans. It is thus desirable to reduce any heating at or close to the lead tip to acceptable and safe levels.

It is known in the art to provide such medical implantable leads with an electrical shielding, in form of a tube of braided wires, which surrounds the coil and which in its proximal end normally is connected to the casing of the monitoring and/or controlling device. However, such shielded medical implantable leads are associated with several disadvantages. The braided shielding will give the medical implantable lead an increased thickness as well as increased rigidity, which normally is not desirable. Moreover, the braided shielding will considerably increase the cost for manufacturing the lead, since it will involve the provision of one additional component, which has to be mounted when assembling the lead. Also, it has appeared that such a braided shielding can not prevent the induction of electrical current to the coiled conductor in a degree that is sufficient to safely permit an individual, having an implanted lead to be exposed to a MRI scanning.

SUMMARY OF THE INVENTION

It is an object of the invention to provide a medical implantable lead having an improved shielding in relation to prior art. More specifically, it is an object to provide a shielded medical implantable lead, by which the shielding can be made with excellent shielding properties and in a cost-saving way.

The invention also relates to a method for manufacturing a medical implantable lead having an electrical shielding, having essentially the same object as above.

The basis of the invention is the insight that the above object may be achieved by manufacturing the conductor coil from one or more wires, each of which has an electrically conducting central wire core provided with a surrounding electrically insulating layer as well as a surrounding electrically conducting shield layer on the outside of the insulating layer. One or more such composite wires, having such a structure, are thereafter helically formed to a close-lapped coil. During operation the wire core is utilized for conduction of signals, normally low frequency signals, between the electrode and the monitoring and/or controlling device, whereas the outer electrically conducting shield layer will function as a shielding for preventing or at least restricting an electromagnetic field from MRI scanning, or from some other type of source, to induce voltage/current into the wire core. At least one end of the shield layer is preferably connected to a casing of the monitoring and/or controlling device for electrical bonding of the shield.

Several advantages may be achieved by a medical implantable lead formed in this way. One advantage is that a wire coil having an electrical shielding according to the invention, may be manufactured to a cost that is not significantly higher than for manufacturing a regular coil without any shielding.

Another advantage is that the shielding properties for a wire coil according to the invention will be improved in relation to a regular shielding in form of a tube of braided wires. This is due to the fact that, since the coil is close-lapped and adjacent loops of the coil will normally be in contact with each other, the conducting path for the induced electric current in the shield layer will be directed in the longitudinal direction of the lead, while the conducting path for the signals in the wire core will be directed in the longitudinal direction of the wires, i.e. nearly 90° in relation to each other since the wire is close-lapped. Small spacings may sometimes be formed between adjacent loops when the lead is bent. However, the small capacitance occurring at the near lying shield layers, will act as a short for the high frequency signals such that electric contact and a conducting path in the longitudinal direction of the lead is nevertheless maintained. However, the possible electric current induced into the outer conducting shield layer, will in its turn have a low susceptibility of inducing its electric current into the wire core since their mutual direction of current flow, will have a large angle, of almost 90° in relation to each other. Moreover, any current induced from the electromagnetic field and from the current in the outer conducting shielding layer into the wire core of the coil will, since it usually concerns electromagnetic fields of very high frequencies, generally radio frequencies of about 30 MHz or more, experience a very high impedance in the coiled conductor which effectively will counteract any induced current in the wire coil. Also, the reactance between adjacent loops of the central wire core will be rather high due to the insulation layer around the wire core, such that the capacitive coupling between adjacent loops will be low which effectively will reduce any current flow due to capacitive coupling.

It is also an advantage that the present invention will result in a less increment of the diameter and the stiffness of the wire coil in comparison with using an ordinary shielding in form of a tube of braided wires, since the shield layer may be formed with a small thickness.

A medical implantable lead according to the invention can be modified in many different ways. A common embodiment of a medical implantable lead comprises two electrically conducting wire coils, which are concentric positioned with one inside the other and which are connected to separate electrodes in the distal end of the lead. One electrode can be in form of a helix, which is connected to the inner wire coil and which is adapted to be screwed into the tissue and accordingly also serves the double function of attaching the distal end of the lead to the organ. The rotating of the helix can optionally be performed by rotating of the inner wire coil in relation to the outer wire coil, as is common knowledge within the art. The outer wire coil, in its turn, can be connected to an indifferent electrode, e.g. a ring formed electrode on the outer circumference of the distal end.

Other embodiments are also conceivable, for example, a medical implantable lead having only one wire coil. In most cases each wire coil forms only one single conductor which, even if it is composed of two or more individual wires, is connected to one single electrode. However, it is within the scope of the invention that a wire coil may contain two or more individual conductor wires, which are co-radially wound to form the wire coil and which are connected to different electrodes. The lead may have more than two electrodes and accordingly also more than two individual conductors. Moreover, the electrodes may be formed in other ways than as a rotatable helix or a ring-formed electrode. For example it can be some other type of penetrating electrode having barbs or the like, or be a contact electrode adapted to abut against a surface of the organ. Also, a fixation means does not need to be penetrating or to have the function of an electrode. Instead the fixation means may be of a type which e.g. is adapted to engage in the trabecular network inside a heart and may have only a fixating function and be combined with a separate electrode, for instance a contact electrode abutting against the surface of the tissue.

If the medical implantable lead includes two or more wire coils, it is within the scope of the invention that only one, all of them, or an arbitrary number of the wire coils are provided with a wire core, a surrounding insulating layer and a surrounding conducting shield layer, according to the invention. The chosen configuration may vary depending on the actual field of application, the required characteristics and the like. Normally, the most critical electrode with regard to heating problems due to induced electromagnetic radiation, is an electrode being in direct contact with the tissue, such as an electrode penetrated into the tissue or abutting against a surface, while an indifferent electrode being only in contact with body fluids, normally is not critical since it often has a rather large surface which will give low current density and the body fluids will cause sufficient cooling of the electrode. However, even if an electrode that is in direct contact with the tissue, is connected to an inner wire coil and there is provided also an outer wire coil, it may be beneficial to arrange the outer wire coil with an insulating layer and a conducting shield layer, according to the invention, in case only one of the wire coils are to be shielded. This is due to the fact that in such case the main part of the electromagnetic field will be absorbed by a shielding being positioned on a comparatively long distance from the most critical inner wire coil, having the result that the inductive as well as the capacitive coupling to the inner wire coil will be rather poor.

Prior art medical implantable leads having two uninsulated wire coils, are normally separated by a flexible tube of an insulating material positioned between the wire coils, in order to maintain the signals in the respective wire coils separated from each other. Using a medical implantable lead according to the invention, in which both of the wire coils are provided with a surrounding insulating layer and a surrounding conducting shield layer, such an intermediate flexible tube may be dispensed with since the inner signal conducting wire cores are insulated from each other. In such a case the inner and outer wire coils will have a common shielding since the outer surrounding conducting shield layer of each wire coil will be in contact with each other. However, it is also conceivable that only one wire coil is provided with a surrounding conducting shield layer whereas the other is provided with only a surrounding insulating layer, as in a hereinafter described and illustrated embodiment.

In an actual embodiment of the invention, the inner conducting wire core may have of diameter of about 0.1-0.15 mm, the surrounding insulating layer may have a thickness of about 0.02-0.1 mm and the surrounding conductive shield layer may have a thickness of about 1 to 50 µm. However, other dimensions are conceivable. The insulating layer could be, for example, an oxide layer, silicon, polyurethane, a combination of those, fluorinated hydrocarbon, e.g. ETFE, polyimide, polyamide, etc. The outer surrounding conducting shield layer may be a metal such as a noble metal, e.g. gold, but also electrical conducting non-metals are conceivable. The insulating layer as well as the shield layer is preferably applied when the wire is in a straight condition and thereafter the wire is wound to form a coil. The shield layer may be applied by means of any suitable method, such as by means of e.g. plasma sputtering, physical vapour deposition, physical vapour decomposition, electrochemical bath, etc.

The thickness of the shield layer will influence the shielding characteristics and is also dependant of the conductance of the material as well as the frequency of the electromagnetic field. By means of a customary braided shield, the characteristics are hard to control. However, with a shield layer according to the invention, the thickness of the shield layer can be controlled within very narrow limits, such that the shielding characteristics may be very close adapted to a specific electromagnetic field, such as from MRI scanning.

The angle between the axial direction of the lead, i.e. the direction which the induced current in the electrical conducting shield layer will have, and the direction of the inner wire core, i.e. the direction of the signals between the electrode and the monitoring and/or controlling device, is dependant of the outer diameter of the wire, the diameter of the wire coil and the number of wires in the wire coil. If, for example, the wire coil has two or more individual wires, the angle will be smaller than if the wire coil only comprises one single wire, since with two or more wires the pitch of the helically wound wires will increase. Generally, it is advantageous the larger the angle is and it is preferred that the angle is at least 70°.

DESCRIPTION OF THE PREFERRED EMBODIMENTS

Figure 1:
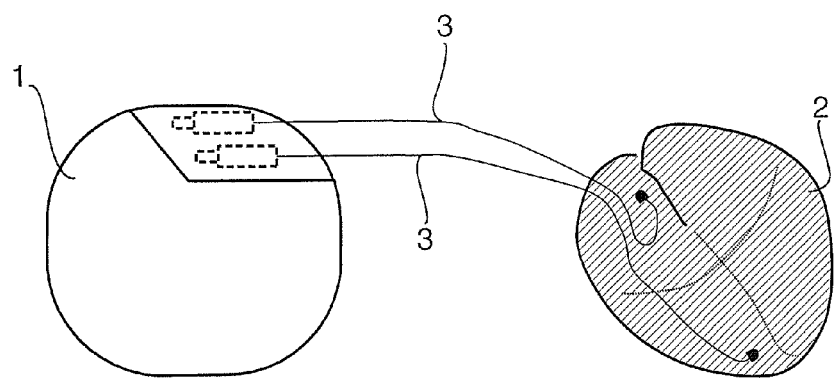
FIG. 1 schematically illustrates the connection of a pacemaker to a heart by means of two medical implantable leads.

Reference is first made to FIG. 1, in which is shown, in a schematic view, the connection of a pacemaker 1 to a heart 2 by means of two medical implantable leads 3. More precisely, one lead is connected to the right atrium and the other lead is connected to the right ventricle of the heart for monitoring and pacing of the heart rate. The pacemaker is normally adapted to be implanted under the skin of the patient, e.g. in the area of one of the collar bones, and the leads can preferably be inserted through a vein leading to the heart. It is to be noted that the reproduction scale of the pacemaker and the heart in the view of FIG. 1 are different for simplified drawing.

Figure 2:
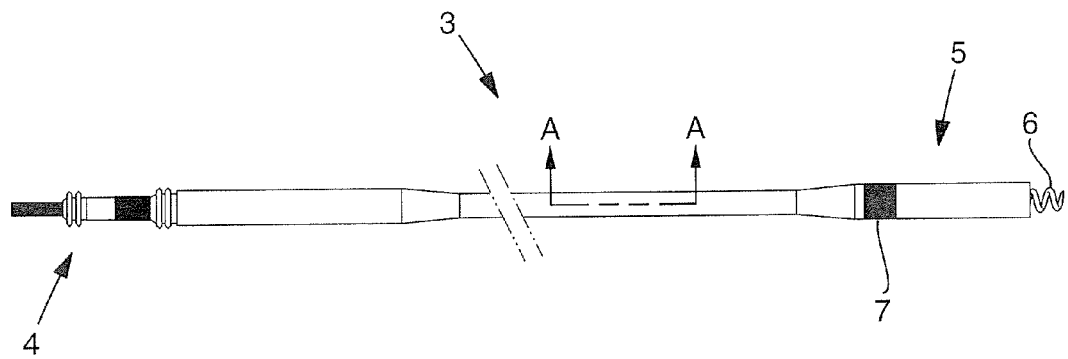
FIG. 2 is a view of a shortened medical implantable lead.

In FIG. 2 is illustrated a medical implantable lead 3, which has been shortened for simplified drawing. The lead has a connector 4 in a proximal end for connection to the pacemaker, an intermediate flexible lead portion, and a so called header 5 in a distal end. The header is provided with a helix 6, which can be screwed out in the axial direction of the lead from a cavity in the distal end of the header. The helix has the function of attaching the distal end of the lead to the heart, by being screwed into the tissue, and also functions as an electrode for receiving and/or transmitting electrical signals from and to the tissue, respectively. The header is also provided with a second electrode 7, a so called indifferent electrode, which is formed as a ring and positioned a small distance from the distal end and has the purpose of forming a complete current path together with the helix.

Figure 3:
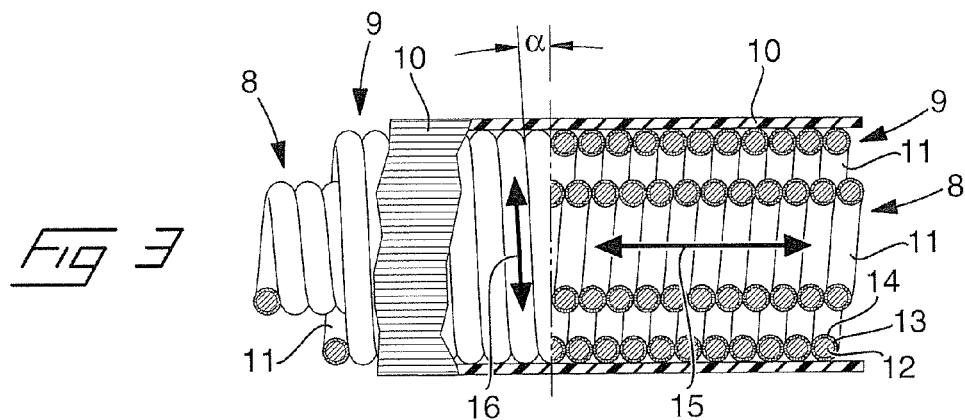
FIG. 3 is a longitudinal view, partly in section and partly cut, through a medical implantable lead according to a first embodiment of the invention.

Reference it then made to FIG. 3, which is a partly longitudinal section and a partly cut through view of a first embodiment of the medical implantable lead along the line A-A in FIG. 2. The lead has an inner wire coil 8, an outer wire coil 9 and an outer protecting, fluidtight and flexible tube 10. The inner as well as the outer wire coils are each comprised of one close-lapped wire 11 which forms an inner bore and, as can be seen, the inner wire coil is concentric positioned within the inner bore of the outer wire coil.

Figure 6:
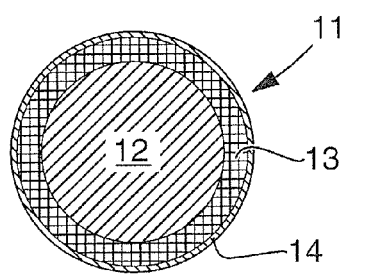
FIG. 6 is a cross-section through a wire having a wire core, an insulating layer and a shield layer in accordance with the present invention.

With reference also to FIG. 6, which illustrates a cross section through the wire 11 of the inner as well as the outer wire coil 8, 9, it can be seen that the wire is composed of an electrically conducting central wire core 12, a surrounding electrically insulating layer 13 and, on the outside of the insulating layer, a surrounding electrically conducting shield layer 14. The central wire core 12 of the inner wire coil 8 is electrically connected to the helix electrode 6, whereas the central wire core 12 of the outer wire coil 9 is connected to the second electrode 7. Since both of the wire coils are close-lapped, the outer electrically conducting shield layer 14 of each of the wires 11 in the inner and outer wire coils 8, 9, respectively, will form a continuous conducting path along the outside as well as the inside of each wire coil. By electrically bonding of this conducting path, formed by the outer conducting shield layers of the wires, to a casing of the pacemaker 1 or the like, an effective shield is obtained for the wire core 12, which is utilized for conducting signals between the pacemaker 1 and the heart 2. The shield layers of the wire coils can both be arranged with electrically bonding or only one of them according to what is most appropriate in each individual case.

Since the shield layers each forms a continuous conducting path along the lead, any induced current from an external electromagnetic field, will induce a high frequency current moving in the axial direction of the lead illustrated by a horizontal bidirectional arrow 15 in FIG. 3. The signals between the pacemaker and the electrodes will proceed within the wire core 12 in the direction of the nearly vertical bidirectional arrow 16 in FIG. 3. This has the effect that the directions of any induced current in the shield layer and the signals inside the wire core will be nearly 90° in relation to each other. In the embodiments of FIGS. 3 and 6, an angle α between the wire and a line being perpendicular to the coil axis, is approximately 3° and consequently the angle between the coil axis and the wire is approximately 87°. This means that any current induced into the shield layer 14 will in its turn be restrained from being induced into the signal conducting wire core 12, as discussed hereinbefore.

Figure 4:
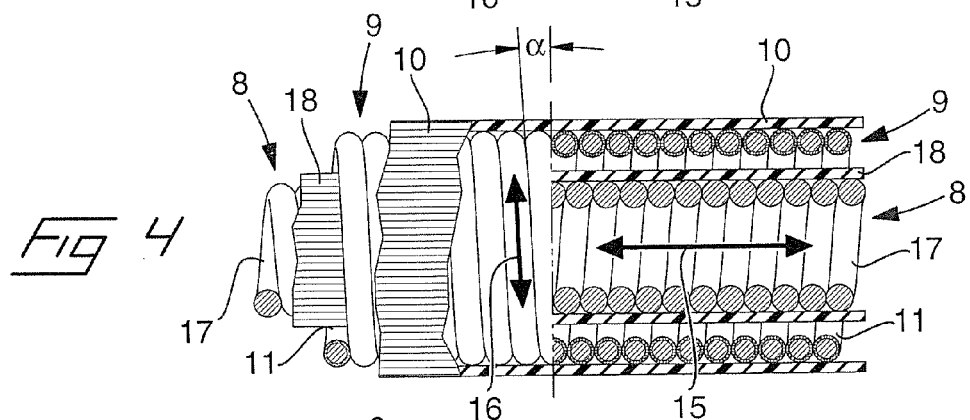
FIG. 4 is a longitudinal view, partly in section and partly cut, through a medical implantable lead according to a second embodiment of the invention.

Reference is then made to FIG. 4, in which is illustrated an embodiment being similar to FIG. 3 except that only the outer wire coil 9 is composed of a wire 11 having a central wire core 12, an insulating layer 13 and a shield layer 14, as in the embodiment according to FIG. 3 and as shown in FIG. 6, while the inner wire coil 8 is composed of a plain electrical conducting wire 17 having neither an insulating layer nor a shield layer. Accordingly, only the outer wire coil 9 is shielded. In order to prevent the inner wire coil 8 from being short-circuited by contact with the shield layer of the outer wire coil, also an inner flexible tube 18 of an electrically insulating material is arranged in the area between the inner and outer wire coils.

Figure 5:
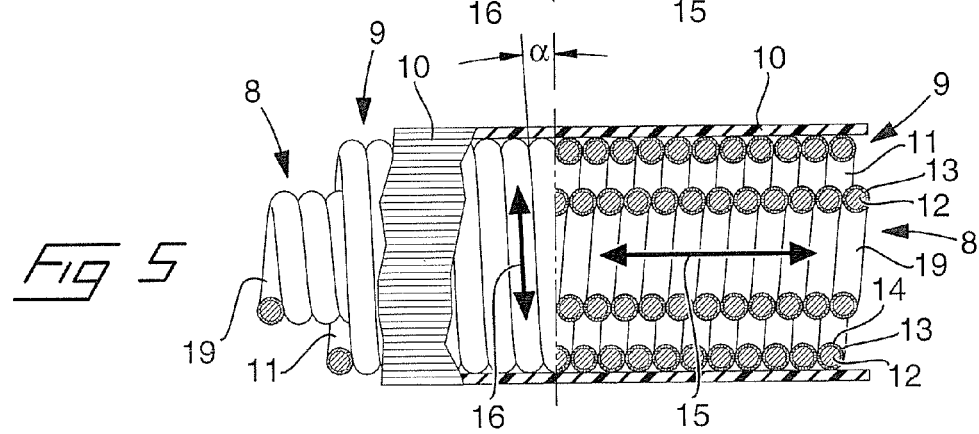
FIG. 5 is a longitudinal view, partly in section and partly cut, through a medical implantable lead according to a third embodiment of the invention.
Figure 7:
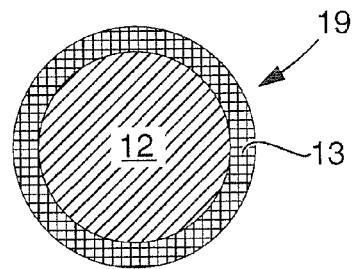
FIG. 7 is a cross-section of a wire having a wire core and an insulating layer, in accordance with the present invention.

In FIG. 5 is illustrated a third embodiment of a medical implantable lead according to the invention. This embodiment comprises an inner wire coil 8, an outer wire coil 9 and an outer protecting, fluidtight and flexible tube 10, i.e. similar to the embodiment of FIG. 3. As in the embodiment in FIG. 3, the outer wire coil 9 is formed of a wire 11 having an inner wire core 12, a surrounding insulating layer 13 and an outer surrounding shield layer 14. However, the inner wire coil 8 is in this embodiment formed of a wire 19, as illustrated in FIG. 7, which only has an inner wire core 12 and a surrounding electrically insulating layer 13. I.e. a surrounding shield layer is missing in this embodiment of the wire. This can be advantageous in so far as in this case the main part of the electromagnetic radiation will be absorbed by the shield layer 14 at the outer wire coil 9. The induced current in the outer wire coil will in its turn have difficulties to be induced over to the inner wire coil, since the induced current in the outer wire coil will be directed in the axial direction of the lead, i.e. in parallel to the arrow 15, while the inner wire coil 8 will only have one conducting direction along the wire core 12, i.e. in parallel to the arrow 16 and almost 90° in relation to the axial direction of the lead, due to the insulating layer 13 and the absence of any shield layer. In comparison to the embodiment according to FIG. 3, the embodiment of FIG. 5 is not formed with an inner coil having a surrounding shield layer conducting an induced current all around the wire core 12, which might further restrain current from being induced into the wire core of the inner coil. On the other hand, in comparison to the embodiment according to FIG. 4, the wire of the inner coil in the embodiment of FIG. 5 is provided with an insulating layer such that the conducting path in the wire core 12 will be in the direction of the wires and not in the axial direction of the lead as in the embodiment of FIG. 4, which also may further restrain current from being induced into the wire core of the inner lead.

It will be apparent to those skilled in the art that the invention disclosed herein is applicable for any type of medical implantable lead, e.g. for an implantable pulse generator such as ICD, neurostimulators etc.

Although modifications and changes may be suggested by those skilled in the art, it is the intention of the inventors to embody within the patent warranted heron all changes and modifications as reasonably and properly come within the scope of their contribution to the art.

We claim as our invention:

1. A medical implantable lead comprising:
   a lead body adapted for implantation in a human or animal, said lead body having a proximal end and a distal end;
   a fixation arrangement located at said distal end of said lead body, said fixation arrangement being adapted to fix the distal end of the lead body in vivo to an organ in the body;
   an electrode arrangement located at said distal end of said lead body and adapted, when the distal end of the lead is fixed by said fixation arrangement to the organ, to receive, or transmit, or receive and transmit, electrical signals with respect to the organ;
   at least one electrical conductor assembly inside said lead body configured to electrically connect at least one of said fixation arrangement and said electrode arrangement with an electrical device at the proximal end of the lead body, said at least one electrical conductor assembly comprising one or more helical sub-assemblies;
   at least one of said one or more helical sub-assemblies comprising a wire coil having a wire core surrounded by an electrically insulating layer, with said electrically insulating layer being surrounded by an electrically conducting shield layer, and said coil being wound with closely-lapped flights that bring respective electrically conducting shield layers of adjacent flights of the coil to be in electrical contact with each other.

2. A medical implantable lead as claimed in claim 1 comprising two helical sub-assemblies, with at least one of said two helical sub-assemblies comprising a wire coil including a central wire core surrounded by an electrically insulating layer that is surrounded by an electrically conducting shield layer.

3. A medical implantable lead as claimed in claim 1 wherein said fixation arrangement is a penetrating fixation arrangement adapted to penetrate into said organ to fix said distal end of said lead body to said organ.

4. A medical implantable lead as claimed in claim 3 wherein said fixation arrangement is formed as a helix adapted to be screwed into said organ.

5. A medical implantable lead as claimed in claim 1 wherein said fixation arrangement forms at least a portion of said electrode arrangement.

6. A medical implantable lead as claimed in claim 1 wherein said at least one helical sub-assembly has a longitudinal axis, and wherein said flights of said wire coil form an angle with said longitudinal axis of at least 70°.

7. A medical implantable lead as claimed in claim 1 wherein said insulating layer has a thickness between 0.02 and 0.1 mm.

8. A medical implantable lead as claimed in claim 1 wherein said electrically conducting shield layer has a thickness between 1 and 50 µm.

9. A medical implantable lead as claimed in claim 1 wherein said at least one helical sub-assembly comprises at least two co-radial wire coils, each having a wire core, an insulating layer and an electrically conducting shield layer.

10. A medical implantable lead as claimed in claim 1 comprising at least two helical sub-assemblies, a first of said at least two helical sub-assemblies comprising at least one wire coil formed by a wire having an inner wire core surrounded by an insulating layer and said insulating layer being surrounded by a shield layer, and a second of said at least two helical sub-assemblies comprising at least one wire coil comprising only an inner wire core and a surrounding insulating layer.

11. A method for manufacturing a medical implantable lead adapted for implantation into a human or animal body for monitoring and/or controlling an organ inside the body, said lead comprising a fixation arrangement at a distal end thereof, adapted to fix the distal end of the lead to the organ, and an electrode arrangement at a distal end of the lead adapted to receive, or transmit, or receive and transmit, electrical signals with respect to the organ, and at least one electrical conductor assembly configured to connect at least one of the fixation arrangement and the electrode arrangement with an electrical device at a proximal end of the lead, said method comprising the steps of forming at least a portion of the conductor assembly by:
   providing an electrically conducting wire core, and covering the electrically conducting wire core with a surrounding electrically insulating layer;
   covering the insulating layer with an electrically conducting shield layer, to form a composite wire;
   winding said composite wire to form a close-lapped coil; and
   assembling the close-lapped coil inside a medical lead body with the central wire core being connected to the electrode arrangement at the distal end of the lead and the outer electrically conducting shield layer being adapted for electrical bonding.

* * * * *